US00PP17814P3

(12) United States Plant Patent
Boyd, III et al.

(10) Patent No.: US PP17,814 P3
(45) Date of Patent: Jun. 19, 2007

(54) **SWEET BAY *MAGNOLIA* NAMED 'PERRY PAIGE'**

(50) Latin Name: ***Magnolia virginiana* var. *australis***
Varietal Denomination: Perry Paige

(76) Inventors: Fernando Campbell Boyd, III, 460 Tenpenny Rd., Morrison, TN (US) 37357; George L. Dodson, III, 802 Greenbrier Dr., Murfreesboro, TN (US) 37130

( * ) Notice: Subject to any disclaimer, the term of this patent is extended or adjusted under 35 U.S.C. 154(b) by 32 days.

(21) Appl. No.: 10/824,299

(22) Filed: Apr. 15, 2004

(65) Prior Publication Data

US 2005/0235388 P1 Oct. 20, 2005

(51) Int. Cl.
*A01H 5/00* (2006.01)

(52) U.S. Cl. ..... Plt./223

(58) Field of Classification Search ..... Plt./223
See application file for complete search history.

*Primary Examiner*—Kent Bell
*Assistant Examiner*—Louanne Krawczewicz Myers

(57) ABSTRACT

A new and distinct *Magnolia virginiana* var. *australis* cultivar, named 'Perry Paige' *Magnolia* that is characterized by its distinct compact and uniform growth habit, evergreen foliage, fragrant citrus scented flowers, and its ability to withstand lower winter temperatures than trees of *Magnolia virginiana* var. *australis* known to the inventors.

4 Drawing Sheets

Latin name: *Magnolia virginiana* var. *australis.*
Varietal denomination: 'Perry Paige'.

FIELD OF THE INVENTION

The present invention comprises a new and distinct cultivar of *Magnolia virginiana* var. *australis,* and referred to by the cultivar name 'Perry Paige'.

BACKGROUND OF THE INVENTION

This new dwarf cultivar of *Magnolia virginiana* var. *australis,* the 'Perry Paige' *magnolia,* was originally discovered by George L. Dodson III, in a group of *Magnolia virginiana* var. *australis* seedlings planted at 3506 Harrison Ferry Road, McMinnville, Tenn. 37110, in 1990. Fernando Campbell Boyd III collected seed on the farm at 3506 Harrison Ferry Road, McMinnville, Tenn. from a group of mature, unnamed *Magnolia virginiana* var. *australis* trees unpatented in the fall of 1988. These seeds were germinated and grown for one growing season at 460 Tenpenny Road, Morrison, Tenn. by Fernando Campbell Boyd III. Then the 1-year-old seedlings were transplanted to the farm on 3506 Harrison Ferry Road, McMinnville, Tenn. in the spring of 1990. It was observed by George L. Dodson III that there was one seedling in this block of *Magnolia virginiana* var. *australis* that exhibited a distinctively different growth habit from the rest of the seedlings in that block of trees. This selected seedling exhibited an attractive, denser, more compact and uniform branch structure. George L. Dodson III evaluated this selected seeding for 5 years.

Those responsible for this new cultivar are George L. Dodson III and Fernando Campbell Boyd III. The initially discovered tree is still growing in a cultivated area at 3506 Harrison Ferry Road, McMinnville, Tenn. 37110.

It was immediately recognized that the new cultivar, 'Perry Paige', was distinctively different in growth from the other seedlings in the block. It had an attractive, denser, more compact branch structure and a slower growth pattern. The other seedlings growing in this population were indicative of the species *Magnolia virginiana* var. *australis* with the exception of the selected individual seedling. While the 'Perry Paige' seedling is shrubby and dense in its growth habit, the other seedlings in the block are tall and leggy in growth. After 14 years, the other seedlings in the block are 20' or more in height and approximately 8' wide and very open in stature. In contrast, the 'Perry Paige' cultivar is approximately 8' tall by approximately 6' wide. After monitoring the initial group for several years, it is apparent that while seedlings of the species *Magnolia virginiana* var. *australis* grow tall and leggy, the *Magnolia virginiana* var. *australis* 'Perry Paige' remains small, compact, dense, and evergreen year after year.

As shown in the photographic drawings, the 'Perry Paige' cultivar is very dense and full of foliage. The 'Perry Paige' cultivar retains its foliage year round in the winter months in Zone 6b, which includes Middle Tennessee, as does the species *Magnolia virginiana* var. *australis*. As shown in more detail in the second and third photographic drawings, the foliage is an olive green on the upper surface and has a silvery sheen on the glaucous underside surface. The leaves are more lanceolate than the species *Magnolia virginiana* var. *australis*, measure approximately 7.6 cm to 16.5 cm in length and 2.85 cm to 4.52 cm in width, and are lustrous. They are not quite as long as, and slightly lighter green in color than the species *Magnolia virginiana* var. *australis.*

As shown in the third photographic drawing, the flower is cup-shaped, 10 to 12 cm across. The flower is white in color. The species *Magnolia virginiana* var. *australis* has more of a creamy white flower. The flower is fragrant with a citrus scent and has 9 to 12 tepals that and are approximately 4.5 cm to 5.5 cm long and 1.9 cm to 3.5 cm wide. The tepals are obovate, separate, involute, entire margin, obtuse apex, and fused at the base. The blooming season is from June to October in Middle Tennessee and the blooms last about a week.

The 'Perry Paige' cultivar is very winter hardy. The tree has proven to be evergreen in a Middle Tennessee climate Zone 6b (USDA Plant Hardiness Zone Map). However, in the severe winter of 1996, the originally discovered plant kept most of its leaves when temperatures reached −10° F. (with a wind chill of −17° F.). In contrast, the other *Magnolia virginiana* var. *australis* in the initial group of seedlings lost most of their leaves, and the low temperatures damaged some of the trees. Thus, the 'Perry Paige' cultivar is more tolerant of extreme cold than the species *Magnolia virginiana* var. *australis*, retaining its foliage year round in Middle Tennessee climate despite temperature of −10° F.

The 'Perry Paige' cultivar is also able to endure drastic changes in the moisture level. The 'Perry Paige' cultivar has been successfully grown without any irrigation. In addition, the originally discovered plant is planted close to a river, and has been completely submerged underwater, because of periodic flooding, at least four times since 1990. Thus, the 'Perry Paige' cultivar thrives in moist soil conditions while tolerating the hot dry conditions of summer.

The 'Perry Paige' cultivar has been successfully asexually propagated. The proven means of asexual propagation has been rooted softwood cuttings. In 1998, Fernando Campbell Boyd III took cuttings from the original selected seedling. These cuttings were placed in a greenhouse at 6294 Manchester Hwy, Morrison, Tenn. Although two-thousand cuttings were stuck the first year, only six rooted. The next year cuttings were only taken off of one of the 'Perry Paige' trees that had been rooted in 1998. The other five 'Perry Paige' *Magnolias* were observed for 2 years. They retained all the characteristics of the original selected seedling. It has been successfully propagated through at least four generations of asexual reporduction, with the highest rooting percentage (as much as 95%) coming from cuttings taken from the newest generation. The 'Perry Paige' *Magnolia* has retained its outstanding unique features throughout each generation of new plants. Each generation has been stable, and reproduced true-to-type plants each and every time the plant has been propagated.

The unique appearance and growth pattern of the 'Perry Paige' cultivar make it well suited for a variety of landscaping uses. It can be used as an evergreen shrub or planted close together to create a novel and attractive hedge to obscure certain areas from view. It is also well suited for use as a foundation plant for larger buildings or in areas that are not large enough for the species *Magnolia virginiana* var. *australis*. Since the 'Perry Paige' *Magnolia* is evergreen with attractive, lustrous, olive green foliage, flowers with a nice fragrance, and is dwarf, it should be a welcome new landscape plant for small and large gardens or various landscape situations. In addition, the unique and attractive 'Perry Paige' *Magnolia* will make a great showpiece for those desiring a rare or unusual *Magnolia virginiana* var. *australis* tree.

SUMMARY OF THE INVENTION

The following characteristics in combination distinguish the new tree named 'Perry Paige' from other cultivars of *Magnolia virginiana* var. *australis*.

1. The 'Perry Paige' cultivar is a dwarf of the *Magnolia virginiana* var. *australis* that has a smaller more bush-like appearance. Young asexually propagated trees, like the initially discovered tree, all tend to grow with a multi-stem trunk. Thus, it is well suited for landscaping applications and areas where the species *Magnolia virginiana* var. *australis* is too large.
2. The 'Perry Paige' *Magnolia* has a longer, more slender leaf than the species *Magnolia virginiana* var. *australis* that adds to its bush-like appearance. In addition, the slender leaves pose less of a clean up problem.
3. The leaf is a lighter green than the species *Magnolia virginiana* var. *australis* which contributes to the 'Perry Paige' *Magnolias's* distinctive and pleasing appearance.
4. The 'Perry Paige' cultivar is more tolerant of extreme cold than the species *Magnolia virginiana* var. *australis*, retaining its foliage year round in a Middle Tennessee climate despite temperatures of −10° F. (with a wind chill of −17° F.).
5. The 'Perry Paige' cultivar is able to endure drastic changes in the moisture level. The originaly discovered plant has been grown, and is thriving, without any irrigation and tolerates the hot dry conditions of summer. In addition, the originally discovered plant has survived being repeatedly submerged by a nearby flooding river.

The 'Perry Paige' cultivar has not been observed under all possible conditions and it is not known how the cultivar might respond to various climates.

BRIEF DESCRIPTION OF THE DRAWINGS

The first photograhic drawing shows the originally discovered 'Perry Paige' plant at fourteen years of age at its home at 3506 Harrison Ferry Road, McMinnville, Tenn.

The second photographic drawing shows a close up of the foliage and an emerging bloom of the 'Perry Paige ' cultivar.

The third photographic drawing shows a close up of the foliage and a fully developed bloom of the 'Perry Paige' cultivar.

The fourth photographic drawing shows a number of second generation 'Perry Paige' rooted cuttings vigorously growing at 6294 Manchester Highway Morrison, Tenn.

DETAILED BOTANICAL DESCRIPTION

The following observations, measurements, and values describe plants grown near Warren County, Tenn. The actual appearance and characteristics of any individual will of course vary due to horticultural practices and local conditions. The tree used for the description is about 14 years old. Color references are made to The Royal Horticultural Society Colour Chart except where terms of ordinary significance are used.

Botanical classification: *Magnolia virginiana* var. *australis*.
Commercial Classification: 'Perry Paige' *Magnolia*.
Origin: Seedling from planted group of seedlings.
Parentage: Seed from mature, unnamed trees of *Magnolia virginiana* var. *australis* (unpatented).
Propagaton: Asexual through softwood cuttings.
Plant:

*Growth rate*.—Slow to medium, average 15 cm per year.
*Form*.—Small multi-stem tree or bush.
*Shape*.—Oval to round.
*Height*.—244 cm in 14 years.
*Spread*.—182 cm in 14 years.
*Density*.—Thick with foliage.

*Trunk size*.—17.8 cm diameter at the base of the trunk at ground level at 14 years.

*Bark*.—Trunk): smooth, color is (197 A RHS) textured with tiny (1 mm) raised oval lenticels.

*Branching arrangement*.—Sub-opposite, bush-like, and multi-stemmed. 'Perry Paige' can be trained to a single stem. Angle of attachment: Ranges from 40 to 45 degrees with 45 being most prevalent.

*Internodal length*.—Mature branches range from 2.3 cm to 4.8 cm.

*Lateral branches*.—On the mature stems the color is (197 A RHS). Typical observed length is up to 15.02 cm, diameter is from 1.3 cm to 6.4 cm. On the new growth of the stem, the color is a mixture of two colors (144 A RHS) and (144 C RHS). The arrangement of leaves is sub-opposite. The length of the new growth stem is 14 cm on average. The diameter of the new growth stem is from 4 mm to 7.6 mm. The internodal length varies from 7.6 mm to 38.1 mm with 20.9 mm being the average.

*Lenticels*.—Tiny, but conspicuous, silver, slightly raised, oval, 1mm.

*Leaves*.—Evergreen.

*Leaf length*.—Petiole 1.3–2.5 cm, average 2.1 cm; Lamina 7.6 cm to 16.5 cm in length and 2.8 cm to 4.5 cm in width. The petioles average 2.8 mm in diameter and are (144 A RHS) in color.

*Average leaf width*.—3.6 cm.

*Leaf shape*.—Lanceolate, with rounded base.

*Leaf margin*.—Entire.

*Leaf texture*.—Smooth on upper and lower surfaces of the leaf; glossy above, silvery-white beneath.

*Leaf quantity*.—Abundant.

*Leaf color*.—Upper side: the color is a mixture of (137 A RHS) and (137 B RHS).

*Lower side*.—Glaucous, the color is a mixture of (188 B RHS) and (188 D RHS).

*Leaf ribs and veins*.—Upper rib surface color (151 A RHS), lower rib surface color (151 B RHS), pinnately veined 12–16 pairs with sub-opposite structure.

*Vegetative buds*.—Terminal, silvery-white pubescence, narrow conical, curved, 3.2 mm to 5.0 mm in diameter by 19.1 mm to 28.6 mm long. The color is a mixture of (192 A RHS) and (192 D RHS). Lateral buds, silvery-white pubescence, narrow conical, curved, 2.6 mm to 3.8 mm in diameter by 3.2 mm to 12.7 long. The color is a mixture of (192 A RHS) and (192 D RHS).

*Leaf apex*.—Acute.

*Base descriptor*.—Rounded.

Flowers:

*Dormant flower buds*.—Terminal, silvery-white pubescence with a color that is a mixture of (192 A RHS) and (192 D RHS), bluntly pointed and averages 9.5 mm in diameter. Average length is 22 mm in length.

*Flower*.—Cup-shaped, 10 to 12 cm across, 2.5 cm in depth, white on the upper surface (155 B RHS), and white on the lower surface (155 C RHS).

*Tepals*.—Number between 9–12; 4.5–5.5 cm long, 1.9–3.5 cm wide; obovate, separate, involute, entire margin, obtuse apex, fused at base. Upper surface texture is smooth. Lower surface texture is smooth.

*Fragrance*.—Fragrant with a light citrus scent.

*Blooming season*.—From June to October in Middle Tennessee.

*Bloom duration*.—About one week on the plant and about two days off the plant depending upon temperature.

*Stamens*.—3 to 4 mm long; about eighty per flower; white (155B RHS) before anthesis, brown (199 A RHS) after; self-fertile.

*Flower arrangement*.—Solitary, terminal bud.

*Pollen amount*.—Moderate.

*Pollen color*. —Yellow (4 C RHS).

*Pistils*.—Number about 80 are are (4 B RHS) in color.

*Anther*.—Number about 80 are are (150 D RHS) in color.

*Stigma* .—Number about 30 and are (149 D RHS) in color.

*Seeds*.—Are (42 A RHS) in color, number approximately 30 per cone like aggregate, triangular shape, and are about 5 to 8 mm in length and 4 mm at the widest diameter.

*Fruit*.—Subglobose to ellipsoid, conelike aggregate of follicles with seeds dispersed througout the follicles of the cone.

*Aggregate of follicles*.—Cone like shape varying from a light green (142 A RHS) to greyed-red (178 A RHS) in color with age and a diameter of 2 cm to 3.3 cm, 2.5 cm being the most common, length 3.5 cm to 4.6 cm, 4 cm being the most common, individual carpels about 1 cm in length, 0.6 cm in diameter, up to 36 carpels per aggregate, each carpel contains one seed.

*Peduncles*.—10–40 cm in length, with 30 cm being the most common, 3.9 mm diameter, coloration is (144 B RHS).

*Disease and pest resistance*.—No known susceptibility to diseases and pests common to *Magnolia virginiana* var. *australis*.

We claim:

1. A new and distinct cultivar of Sweet Bay *Magnolia* tree named 'Perry Paige' as illustrated and described herein.

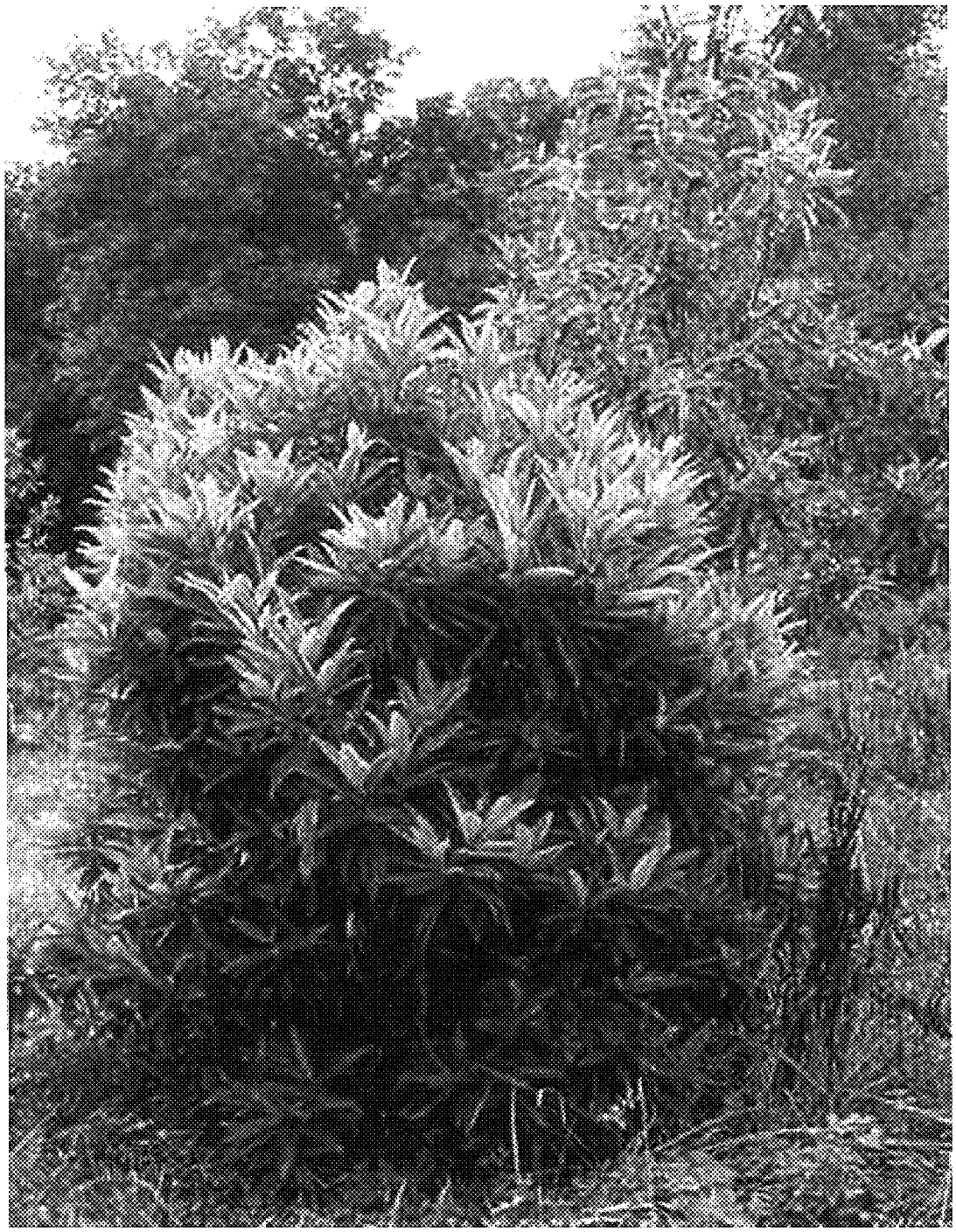

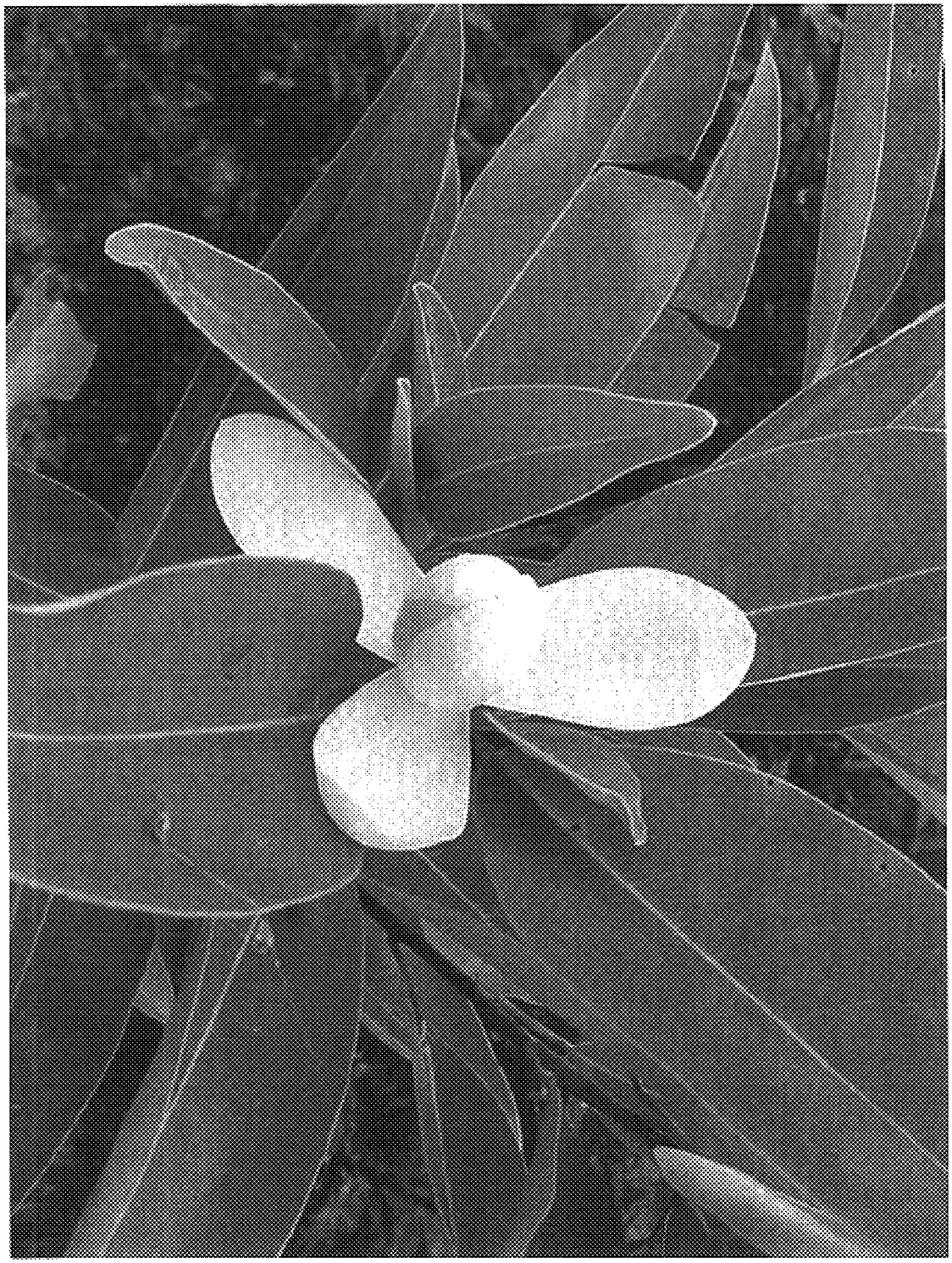

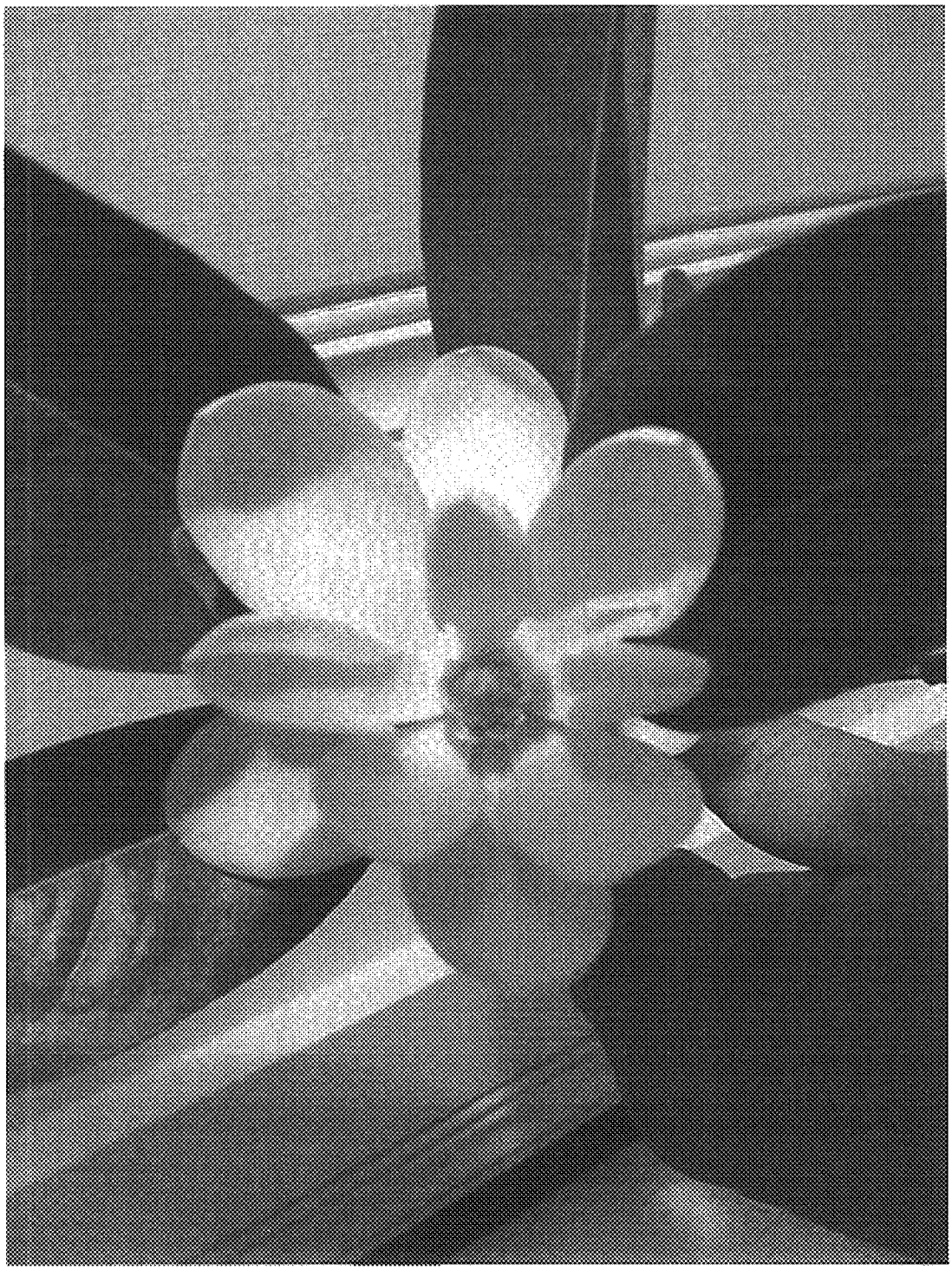

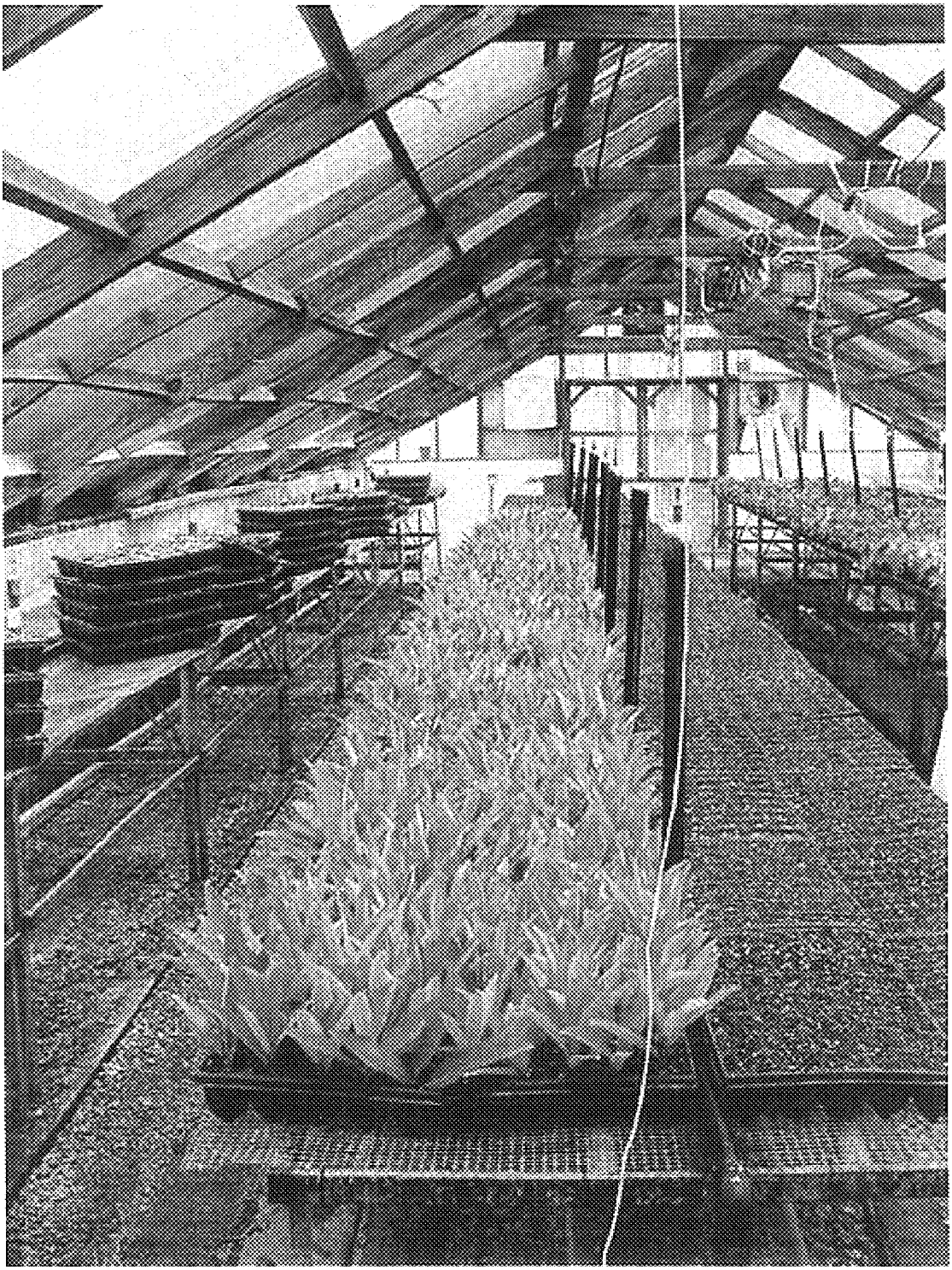

* * * * *